(12) United States Patent
Rao et al.

(10) Patent No.: US 11,986,288 B2
(45) Date of Patent: *May 21, 2024

(54) COLOROMETRIC SENSOR FOR THE NON-INVASIVE SCREENING OF GLUCOSE IN SWEAT IN PRE AND TYPE 2 DIABETES

(71) Applicant: MEDTRONIC MINIMED, INC., Northridge, CA (US)

(72) Inventors: Ashwin K. Rao, West Hills, CA (US); Rebecca K. Gottlieb, Culver City, CA (US); Quyen Ong, Arcadia, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 654 days.

This patent is subject to a terminal disclaimer.

(21) Appl. No.: 15/912,473

(22) Filed: Mar. 5, 2018

(65) Prior Publication Data
US 2018/0303388 A1    Oct. 25, 2018

Related U.S. Application Data

(60) Provisional application No. 62/467,653, filed on Mar. 6, 2017.

(51) Int. Cl.
*A61B 5/145* (2006.01)
*A61B 5/1477* (2006.01)
(Continued)

(52) U.S. Cl.
CPC ...... *A61B 5/14532* (2013.01); *A61B 5/14517* (2013.01); *A61B 5/1486* (2013.01);
(Continued)

(58) Field of Classification Search
CPC ............ A61B 5/14532; A61B 5/14517; A61B 5/1477; A61B 5/1486; A61B 5/14539;
(Continued)

(56) References Cited

U.S. PATENT DOCUMENTS

| 4,755,173 A | 7/1988 | Konopka et al. |
| 5,391,250 A | 2/1995 | Cheney, II et al. |

(Continued)

FOREIGN PATENT DOCUMENTS

| WO | 00/14535 | 3/2000 | |
| WO | WO-0014535 A1 * | 3/2000 | ......... A61B 5/14514 |

(Continued)

OTHER PUBLICATIONS

PCT International Search Report & Written Opinion dated Jun. 7, 2018 for PCT Application No. PCT/US2018/021179.
(Continued)

*Primary Examiner* — Blaine Lankford
*Assistant Examiner* — Lauren K Van Buren
(74) *Attorney, Agent, or Firm* — GATES & COOPER LLP

(57) ABSTRACT

Described here are patches and methods for measuring glucose in sweat (and tears and the like). In general, the patches comprise an adhesive layer adapted to bond to skin of an individual, a substrate layer disposed over the adhesive layer and comprising a glucose sensing complex including a chromogen that changes color in the presence of certain concentrations of glucose, and a cover. In typical embodiments, the substrate layer has elements formed to direct and accumulate sweat that migrates from the skin of the individual to the glucose sensing complex. Methods of using the invention can comprise cleaning the skin surface, collecting sweat in a patch comprising this microfluidic constellation of elements, and observing concentrations of glucose collected in the sweat, for example either visually, or by using a smartphone or other computer processing device.

17 Claims, 13 Drawing Sheets

(51) Int. Cl.
*A61B 5/1486* (2006.01)
*G01N 33/52* (2006.01)
*G01N 33/66* (2006.01)
*A61B 5/00* (2006.01)
*C07K 14/62* (2006.01)
*C12Q 1/00* (2006.01)

(52) U.S. Cl.
CPC ........... *G01N 33/526* (2013.01); *G01N 33/66* (2013.01); *A61B 5/14539* (2013.01); *A61B 5/14546* (2013.01); *A61B 5/1477* (2013.01); *A61B 5/6833* (2013.01); *C07K 14/62* (2013.01); *C12Q 1/006* (2013.01)

(58) Field of Classification Search
CPC .............. A61B 5/6833; A61B 5/14546; A61B 2560/0412; A61B 5/6832; G01N 33/526; G01N 33/66; G01N 2800/042; C07K 14/62; C12Q 1/006; C12Q 1/54
See application file for complete search history.

(56) References Cited

U.S. PATENT DOCUMENTS

| | | | |
|---|---|---|---|
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,251,083 | B1 | 6/2001 | Yum et al. |
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 2002/0026111 | A1* | 2/2002 | Ackerman ......... A61B 5/14532 600/347 |
| 2006/0188443 | A1* | 8/2006 | Redmond .......... A61K 49/0004 424/9.1 |
| 2007/0027383 | A1 | 2/2007 | Peyser et al. |
| 2007/0123819 | A1 | 5/2007 | Mernoe et al. |
| 2009/0270704 | A1* | 10/2009 | Peyser ............... A61B 5/14532 600/346 |
| 2010/0045993 | A1 | 2/2010 | Martini et al. |
| 2010/0063372 | A1 | 3/2010 | Potts et al. |
| 2010/0160861 | A1 | 6/2010 | Causey, III et al. |
| 2013/0172699 | A1* | 7/2013 | Rebec .................. A61B 5/1459 600/316 |
| 2014/0058225 | A1* | 2/2014 | Markle ................ A61B 5/1459 600/316 |
| 2014/0324004 | A1* | 10/2014 | Song ...................... A61L 15/56 604/359 |

FOREIGN PATENT DOCUMENTS

| | | |
|---|---|---|
| WO | 00/57177 | 9/2000 |
| WO | 2011/008581 | 1/2011 |
| WO | 2016025468 A2 | 2/2016 |

OTHER PUBLICATIONS

European Communication Pursuant to Article 94(3) EPC dated Mar. 3, 2023 for EP Application No. 1871744.2.
Chinese Second Office Action dated Jun. 30, 2022 for Chinese Patent Application No. 201880019595.1.

* cited by examiner

Mediators:

Ferricyanide

Meldola's Blue

Methylene blue menadione

COLOROMETRIC SENSOR FOR THE NON-INVASIVE SCREENING OF GLUCOSE IN SWEAT IN PRE AND TYPE 2 DIABETES

CROSS-REFERENCE TO RELATED APPLICATIONS

This application claims priority under Section 119(e) from U.S. Provisional Application Ser. No. 62/467,653, filed Mar. 6, 2017, the contents of which are incorporated herein by reference.

TECHNICAL FIELD

The present invention relates to glucose sensors for the diagnosis of diabetes and methods and materials useful for making and using them.

BACKGROUND OF THE INVENTION

Diabetes is a life-threatening disease with broad complications, which include blindness, kidney disease, nerve disease, heart disease, amputation, and stroke. The American Diabetes Association reports that approximately 7.8% of the population in the United States have diabetes, and that this number is growing at a rate of 12-15% per annum. The Association further reports that diabetes is the seventh leading cause of death in the United States. Diabetes is believed to be the leading cause of new cases of blindness in individuals between the ages of 20 and 74; approximately 12,000-24,000 people per year lose their sight because of diabetes. Diabetes is also the leading cause of end-stage renal disease, accounting for nearly 44% of new cases. Nearly 60-70% of people with diabetes have mild to severe forms of diabetic nerve damage which, in severe forms, can lead to lower limb amputations. People with diabetes are 2-4 times more likely to have heart disease and to suffer strokes than people without diabetes.

Diabetes results from the inability of the body to produce or properly use insulin, a hormone needed to convert sugar, starches, and the like into energy. There are two major types of diabetes: Type 1 and Type 2. Type 1 diabetes (also known as juvenile diabetes) is caused by an autoimmune process destroying the beta cells that secrete insulin in the pancreas. Type 1 diabetes most often occurs in young adults and children. People with Type 1 diabetes must take daily insulin injections to stay alive. Type 2 diabetes is a metabolic disorder resulting from the body's inability to make enough, or properly to use, insulin. Type 2 diabetes is more common, accounting for 90-95% of diabetes. In the United States, Type 2 diabetes is nearing epidemic proportions, principally due to an increased number of older Americans and a greater prevalence of obesity and sedentary lifestyles.

Insulin is a hormone that allows glucose to enter cells and feed them. In diabetics, glucose cannot enter the cells. Consequently, glucose builds up in the blood to toxic levels. For this reason, glucose concentrations are monitored to diagnose and manage diabetes. A number of non- or minimally-invasive glucose monitoring techniques have been investigated, some of which focus on the measurement of glucose on the skin surface or in interstitial fluid. For example, U.S. Pat. No. 4,821,733 to Peck describes a process to detect an analyte that has come to the skin surface via diffusion. Similarly, U.S. Pat. No. 6,503,198 to Aronowitz describes a transdermal system for analyte extraction from interstitial fluid. U.S. Pat. No. 5,140,985 to Schroeder et al. describes a non-invasive glucose monitoring unit, which uses a wick to absorb the sweat and electrochemistry to make glucose measurements. Similarly, U.S. Pat. No. 5,036,861 to Sembrowich et al. describes glucose monitoring technology based on analyzing glucose on the skin surface from a localized, modified sweat response. In a like manner, U.S. Pat. No. 5,638,815 to Schoendorfer describes a dermal patch to be worn on the skin for increasing the concentration of an analyte expressed through the skin in perspiration, to a conveniently measurable level. However, in view of the low concentrations of glucose in sweat and the low volumes of sweat that are readily available, these conventional patches that attempt to measure glucose from sweat have a number of limitations.

Because disorders such as diabetes are chronic and have ongoing detrimental effects, there is a need for effective and economical methods of determining a subject's glucose levels in order to, for example, diagnose diabetes as early as possible. Embodiments of the invention disclosed herein meet this as well as other needs.

SUMMARY OF THE INVENTION

In brief, the present invention overcomes certain drawbacks and shortcomings of conventional systems for measuring glucose levels by providing a novel transdermal system for determining glucose concentrations in sweat and methods concerning the same. In accordance with the present invention, the novel noninvasive transdermal patches disclosed herein provide for sample collection and detection in the form of a simple, easy-to-use, integrated system which is low-cost and suitable for convenient use by non-medical personnel. Moreover, because the novel transdermal systems of the present invention are noninvasive and painless as compared to the invasive techniques generally utilized heretofore (for example a finger prick or finger lance), individual compliance will be enhanced, while the risk of disease transmission and infection will be simultaneously reduced.

The invention disclosed herein has a number of embodiments. One embodiment is a sweat patch glucose sensor comprising an adhesive layer adapted to bond to skin of an individual, wherein the adhesive layer comprises an opening adapted to allow sweat to migrate from the skin of the individual to a glucose sensing complex within the glucose sensor, a substrate layer disposed over the adhesive layer and comprising a glucose sensing complex, wherein substrate layer accumulates sweat that migrates from the skin of the individual into the sensor. In this sensor, the glucose sensing complex comprises an enzyme complex that reacts with glucose, for example glucose oxidase, glucose dehydrogenase or a hexokinase/glucose-6-phosphate complex. The sensor further comprises a colorimetric indicator (e.g. a chromogen) in operable contact with the glucose sensing complex that changes color following reaction of glucose with the enzyme complex. Optionally, for example, the colorimetric indicator is disposed in the sensor that provides a qualitative indication of hyperglycemia, and for example is adapted to change color when the concentration of glucose in sweat exceed a preselected point, for example when the concentration of glucose is greater than 1.8 mg/dL. This sensor embodiment further includes a spacer layer disposed over the substrate layer, wherein the spacer layer comprises a port that allows visualization of the glucose sensing complex in the substrate layer, as well as a cover layer disposed over the spacer layer, wherein the cover layer comprises a port that allows visualization of the glucose sensing complex in substrate layer.

In embodiments of the invention, the sensor elements disclosed herein are disposed in locations and amounts that provide the sensors with a number of desirable features. For example, in certain embodiments of the invention, the elements are disposed in the system in locations and amounts so that the glucose sensing complex is adapted to measure very low volumes of glucose, for example glucose in volumes of sweat that are between 5 microliters and 25 microliters. Typically in the sensors of the invention, a region of the substrate layer in which the glucose sensing complex is disposed further comprises a preloaded amount of glucose that is disposed in the sensor to form a threshold concentration of glucose in an aqueous environment in which the glucose sensing complex is disposed. In certain embodiments of the invention, a region of the substrate layer in which the glucose sensing complex is disposed comprises preloaded buffering compounds adapted to modulate the pH at which the glucose sensing complex senses glucose.

Sensors of the invention can include additional elements that facilitate the user interface with the sensor, for example a wetness or volume indicator that indicates when sufficient sweat has accumulated for the glucose sensing reaction. Similarly, some embodiments of the invention can include a color key that indicates the expected color of the colorimetric indicator when concentrations of glucose in the sweat of the individual are at a certain level, for example when concentrations of glucose are greater than 1.8 mg/dL. Similarly, some embodiments of the invention can include a pH indicator that indicates the pH of the glucose sensing reaction. These elements are typically disposed in the top of the sensor where they are highly visible to a user. In addition, embodiments of the sensor can include an adhesive transparent layer that can be disposed over the cover layer, and which functions to inhibit the evaporation of sweat during the sensing process.

A related embodiment of the invention is a method of making a glucose sensor for detecting glucose in sweat, the method comprising forming an adhesive layer adapted to bond to skin of an individual, wherein the adhesive layer comprises an opening adapted to allow sweat to migrate from the skin of the individual to a glucose sensing complex within the glucose sensor. This method further comprises forming a substrate layer over the adhesive layer, one that comprises a glucose sensing complex and is adapted to direct the flow of and/or accumulate sweat that migrates from the skin of the individual in to the sensor. In this embodiment, the glucose sensing complex comprises an enzyme complex that reacts with glucose and comprises: glucose oxidase, glucose dehydrogenase or a hexokinase/glucose-6-phosphate complex and a colorimetric indicator that changes color following reaction of glucose with the enzyme complex. Optionally in these embodiments, the colorimetric indicator in the glucose sensing complex is a first color when the concentration of glucose in the sweat of the individual is less than 1.8 mg/dL, and a second color when the concentration of glucose is greater than 1.8 mg/dL. These methods further comprise forming a spacer layer disposed over the substrate layer, wherein the spacer layer is formed to comprise a port that allows visualization of the glucose sensing complex in the substrate layer; and also forming a cover layer over the spacer layer, wherein the cover layer is formed to comprise a port that allows visualization of the glucose sensing complex in substrate layer.

These methods of making a glucose sensor can include forming other elements on the sensor, for example a wetness indicator that indicates when sufficient sweat has accumulated for the glucose sensing reaction; and/or a color key that shows the expected color when the concentration of glucose in the sweat of the individual is less than 1.8 mg/dL and/or the expected color when the concentration of glucose is greater than 1.8 mg/dL; and/or a pH indicator that indicates the pH of the aqueous solution in which glucose is sensed. Optionally in these methods, a region of the substrate layer is constructed to comprise a preloaded concentration of glucose in amounts adapted to form a threshold concentration of glucose in an aqueous environment in which the glucose sensing complex is disposed (e.g. so as to offset the problems with low glucose concentrations in sweat and obtain a more pronounced color change of a chromogen). In certain embodiments of the invention, the method further comprises forming hydrophobic regions on the glucose sensor that are adapted to modulate the flow of sweat through the glucose sensor. Typically, the glucose sensor is formed to measure glucose in volumes of sweat that are between 5 microliters and 25 microliters; and/or to indicate when the concentration of glucose in the sweat of a user is greater than 1.8 mg/dL.

Yet another embodiment of the invention is a method of detecting hyperglycemia in an individual, comprising the steps of wiping skin of the individual to remove contaminants at a site at which the sensor will be adhered and then adhering a patch glucose sensor as disclosed herein to the skin of the individual. These methods can further comprise disposing a transparent sheet over the sensor, wherein the transparent sheet comprises an adhesive, and is formed from a material selected for its ability to inhibit the evaporation of sweat during glucose sensing. Typically, in these methods, the sensors used include additional elements that facilitate the user interface with the sensor, for example a wetness indicator that indicates when sufficient sweat has accumulated for the glucose sensing reaction. Similarly, some embodiments of the invention can include a color key that indicates the color of the colorimetric indicator when concentrations of glucose in the sweat of the individual are at a certain level, for example when concentrations of glucose are greater than 1.8 mg/dL. Similarly, some embodiments of the invention can include a pH indicator that indicates the pH of the glucose sensing reaction. With such sensors, the methods can further comprise having the user visualize and compare a sample color to standard color chart, for example by taking a photograph of the glucose sensing complex and the predetermined color key (and/or pH key) with a smartphone so as provide a computer readable comparison of the color of the colorimetric indicator (or pH) with that of the predetermined color indicator (e.g. using a smartphone to take photographs of the sensor readout at t=0 and t=10 min).

Another embodiment of the invention is a composition of matter comprising a glucose sensing enzyme complex that reacts with glucose and comprises: glucose oxidase, glucose dehydrogenase or a hexokinase/glucose-6-phosphate complex in operable contact with a colorimetric indicator that changes color following reaction of glucose with the enzyme complex; and also a predefined concentration of glucose adapted to form a threshold concentration of glucose in an aqueous environment as the glucose sensing complex senses glucose. Typically, these elements are disposed in locations and amounts so that the glucose sensing complex is adapted to determine the concentrations of glucose in aqueous solutions having a volume between 5 and 25 microliters.

In one exemplary embodiment of the invention, the glucose sensing complex comprises glucose oxidase, and the colorimetric indicator comprises a Trinder reagent comprising an aminoantipyrine (such as 4-aminoantipyrine or the like) and a phenol (such as p-hydroxybenzene or the like).

In another exemplary embodiment of the invention, the glucose sensing complex comprises glucose dehydrogenase and the colorimetric indicator comprises a water-soluble tetrazolium salt, and the method further comprises combining the glucose sensing complex with nicotinamide adenine dinucleotide (NAD) and a 1-methoxy-5-methylphenazium methylsulfate. In another exemplary embodiment of the invention, the glucose sensing complex comprises a hexokinase/glucose-6-phosphate complex and the colorimetric indicator comprises a water-soluble tetrazolium salt, and the method further comprises combining the glucose sensing complex with nicotinamide adenine dinucleotide (NAD) and a 1-methoxy-5-methylphenazium methylsulfate.

A related embodiment of the invention is a method of making a composition that measures glucose concentrations between 0 mg/dL and 5 mg/dL in small volumes of liquid (e.g. 5-25 microliters) by exhibiting a first color when disposed in aqueous solutions having a first concentration of glucose, and a second color when disposed in aqueous solutions having a second higher concentration of glucose. The method typically comprises combining together a glucose sensing enzyme complex that reacts with glucose and comprises: glucose oxidase, glucose dehydrogenase or a hexokinase/glucose-6-phosphate complex; and a colorimetric indicator that changes color following reaction of glucose with the enzyme complex. Optionally the methods further comprise combining the glucose sensing enzyme complex with a predefined concentration of glucose adapted to form a threshold concentration of glucose in an aqueous environment as the glucose sensing complex senses glucose.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION OF THE INVENTION

Figure 1:
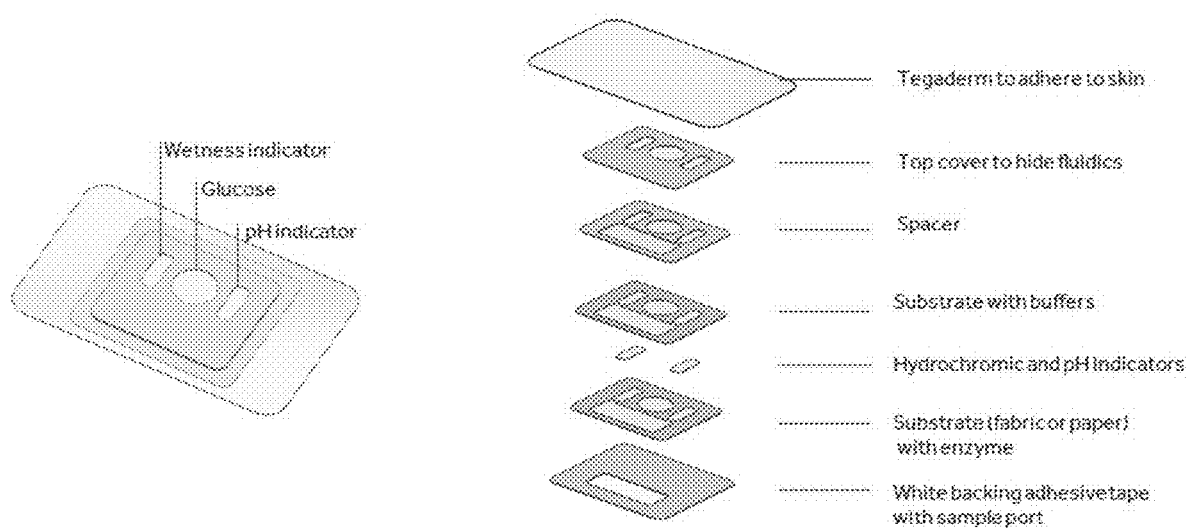
FIG. 1 provides a cartoon schematic of an embodiment of the sweat patch glucose sensor as it appears on skin (left panel) as well as an expanded view showing various elements of this sensor embodiment (right panel).
Figure 2:
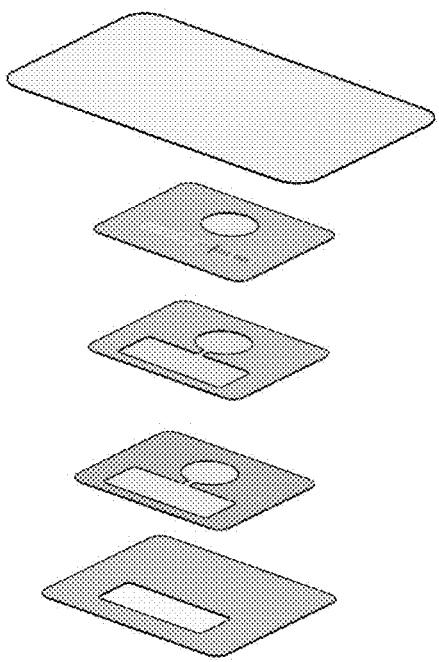
FIG. 2 provides a cartoon schematic of an embodiment of a simple sweat patch glucose sensor in an expanded view showing various elements of this minimal sensor embodiment.

Unless otherwise defined, all terms of art, notations, and other scientific terms or terminology used herein are intended to have the meanings commonly understood by those of skill in the art to which this invention pertains. In some cases, terms with commonly understood meanings may be defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

All numbers recited in the specification and associated claims that refer to values that can be numerically characterized with a value other than a whole number (e.g. the diameter of a circular disc) are understood to be modified by the term "about". Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Furthermore, all publications mentioned herein are incorporated herein by reference to disclose and describe the methods and/or materials in connection with which the publications are cited (e.g. U.S. Patent Publication Nos. 20020019055, 20060004271, 20090270704, 20100063372 and 201000049016). Publications cited herein are cited for their disclosure prior to the filing date of the present application. Nothing here is to be construed as an admission that the inventors are not entitled to antedate the publications by virtue of an earlier priority date or prior date of invention.

Further the actual publication dates may be different from those shown and require independent verification.

The term "sensor" for example in "glucose sensor," is used in its ordinary sense, including, without limitation, refers to means used to detect a compound such as glucose. A "sensor system" includes, for example, elements, structures and architectures (e.g. specific 3-dimensional constellations of elements) designed to facilitate sensor use and function. Sensor systems can include, for example, compositions disposed in locations and amounts that generate selected material or functional properties, as well as elements used in signal detection and analysis.

The determination of physiological analytes in sweat has a number of advantages including non-invasive and painless sample collection. Sweat can be collected painlessly from locations such as the forehead, back of the neck, lower back, wrist, palm, sole of the feet and the like. Unfortunately, there are challenges in assaying this fluid because sweat typically includes very low concentration levels of analytes of interest. Analyte sweat detection therefore requires high sensitivity and selectiveness to provide significant results. The sweat sensors disclosed herein provide non-invasive, self-screening tools useful to raise awareness pre- and type 2 diabetes using sweat samples (alternatively saliva, tears or urine) which are specifically adapted to detect low glucose levels (glucose levels in tears and sweat range between 0-5 mg/dL), a concentration range of glucose that is beyond the lower detection limit of commercially available BG strips and urine strips. Using microfluidics technology, the sweat sensors can provide preliminary information that leads to a further follow up visit with a physician. This sensor therefore allows population screening in a qualitative manner.

As illustrated in detail below, the invention disclosed herein has a number of embodiments. One embodiment is a sweat patch glucose sensor comprising an adhesive layer adapted to bond to skin of an individual, wherein the adhesive layer comprises an opening adapted to allow sweat to migrate from the skin of the individual to a glucose sensing complex within the glucose sensor, a substrate layer disposed over the adhesive layer and comprising a glucose sensing complex, wherein substrate layer directs the flow of and/or accumulates sweat that migrates from the skin of the individual into the sensor. In this sensor, the glucose sensing complex comprises an enzyme complex that reacts with glucose, for example glucose oxidase, glucose dehydrogenase or a hexokinase/glucose-6-phosphate complex. The sensor further comprises a colorimetric indicator that changes color following reaction of glucose with the enzyme complex. This sensor embodiment includes a spacer layer disposed over the substrate layer, wherein the spacer layer comprises a port that allows visualization of the glucose sensing complex in the substrate layer; as well as a cover layer disposed over the spacer layer, wherein the cover layer comprises a port that allows visualization of the glucose sensing complex in the substrate layer. Layered elements of the sensor such as the adhesive layer can be formed from adhesive patches and patch transfer tape, Papilio (Color Laser Clear Glossy Polyester Film) as well as the use of printable polyester sheets to laminate layers and create constructs. These sheets can be printable and have adhesive on one side. Printable properties can be used for masking un-desired areas and have a color viewing window.

Illustrative colorimetric indicators (chromogens) useful in embodiments of the invention include Trinder reagents, water soluble tetrazolium salts such as WST-1, WST-8, MTT, MTS, as well as resazurin (reduced product of resazurin fluoresces to green light). Optionally the colorimetric indicator is disposed in the sensor in a manner that provides a qualitative indication of hyperglycemia, and for example is adapted to change color when the concentration of glucose in sweat exceed a preselected point, for example when the concentration of glucose is greater than 1.8 mg/dL. Some embodiments of the invention can enhance chromogen visualization by for example, by increasing optical density by using thicker paper or use of polymeric base to increase thickness of a coating, or the use of binding agents such as hydroxypropylcellulose (see, e.g. U.S. Pat. No. 8,574,896). Alternatively, one can use chemicals dried on a transfer paper that can be applied akin to a child's temporary tattoo (the chemicals can be transferred onto the stamp to enhance the color, or fix the color, or terminate the reaction). Alternatively, one can use computer/phone image processing to facilitate chromogen visualization.

In embodiments of the invention, the sensor elements such as the compositions disclosed herein are disposed in locations and amounts that provide the sensors with a number of desirable features. For example, in certain embodiments of the invention, the elements are disposed in the system in locations and amounts so that the glucose sensing complex is adapted to measure very low volumes of glucose, for example glucose in volumes of sweat that are between 5 microliters and 25 microliters. Typically in the sensors of the invention, a region of the substrate layer in which the glucose sensing complex is disposed further comprises a preloaded glucose adapted to form a threshold concentration of glucose in an aqueous environment in which the glucose sensing complex is disposed.

The pH of sweat can vary from 3.5-7.5, while certain glucose sensing complexes work best in the range of pH 7.5-9. An optimized sweat pH in embodiments of the invention can be achieved by using pre-dried buffers (such as TRIS, PBS, HEPES and the like) on the substrate, or by alternatively using ion exchange materials coated on the paper. Consequently, in certain embodiments of the invention, a region of the substrate layer in which the glucose sensing complex is disposed comprises preloaded buffering compounds adapted to modulate the pH at which the glucose sensing complex senses glucose. Other embodiments of the invention comprise an anion exchange paper (e.g. DE81, GE) to convert the sweat to hydroxide anions which help buffer the sweat (pH 7-9). Such embodiments of the invention can include pH paper or the like to indicate if pH of the sweat sample is optimal.

Optimal sweat volume is needed for the glucose sensing reaction. Sensors of the invention can therefore include additional elements that facilitate the user interface with the sensor, for example a volume/wetness indicator that indicates when sufficient sweat has accumulated for the glucose sensing reaction. Consequently, the use of a wetness indicator can help determine when desired sample volume has been achieved. One example of a wetness indicator is hydrochromic ink which becomes transparent upon being wetted. Similarly, some embodiments of the invention can include a color key that indicates the expected color of the colorimetric indicator when concentrations of glucose in the sweat of the individual are at a certain level, for example when concentrations of glucose are greater than 1.8 mg/dL. Similarly, some embodiments of the invention can include a pH indicator that indicates the pH of the glucose sensing reaction. These elements are typically disposed in the top of the sensor where they are highly visible to a user. In addition, embodiments of the sensor can include an adhesive transparent layer that can be disposed over the cover layer, and which functions to inhibit the evaporation of sweat.

In certain embodiment of the invention, the sensor (e.g. the substrate layer) comprises hydrophilic regions and hydrophobic regions adapted to modulate the flow of sweat through the glucose sensor. This creates a fluidic path that directs sweat to a reagent zone and to avoid dye to leaching onto patient's skin. This can create a fluidic flow that has a positive flow from a sweat collection window/opening to reaction zone comprising the glucose sensing complex which is exposed to air. Optionally, the substrate layer and/or the spacer layer and/or other layers are formed from adsorbent material(s) adapted to wick sweat from the skin of the individual through the glucose sensor. Certain embodiments of the sensor include layers formed from hydrophobic elements. Embodiments of the invention use backing on a sensor layer with a hole on it to wick sweat from underneath the sensor. Embodiments of the invention further use adhesives on the edges of one or more sensor layers to avoid sweat external to sensor from contaminating a sample.

The substrate and other layers can comprise a fabric (woven or non-woven), filter paper, nitrocellulose, cellulose, polyester, materials which can be wax printed to create hydrophobic regions (see, e.g. R. M. Crooks et. al., Langmuir 2014, 30, 7030-7036). Embodiments of the invention may also comprise a sweat-permeable membrane configured to act as a barrier to epidermal contaminants and glucose brought to the skin surface via diffusion. The sweat-permeable membrane may be made of a material that is generally occlusive, but allows sweat to pass therethrough or may be made of a liquid polymer that cures when exposed to oxygen and leaves openings over the sweat gland pores. Other alternative sweat-permeable membranes may also be used. Examples of sweat permeable membranes include hydrophobic materials such as petrolatum, paraffin, mineral oils, silicone oils, vegetable oils, waxes, a liquid polymer coating, silicon polymers, inorganic membranes, a membrane filter such as polycarbonate track-etch membrane filters, and the like.

A related embodiment of the invention is a method of making a glucose sensor for detecting glucose in sweat, the method comprising forming an adhesive layer adapted to bond to skin of an individual, wherein the adhesive layer comprises an opening adapted to allow sweat to migrate from the skin of the individual to a glucose sensing complex within the glucose sensor. This method further comprises forming a substrate layer over the adhesive layer, one that comprises a glucose sensing complex and is adapted to direct the flow of and/or accumulate sweat that migrates from the skin of the individual in to the sensor. In this embodiment, the glucose sensing complex comprises an enzyme complex that reacts with glucose and comprises: glucose oxidase, glucose dehydrogenase or a hexokinase/glucose-6-phosphate complex and a chromogen that changes color following reaction of glucose with the enzyme complex. Optionally in these embodiments, the colorimetric indicator in the glucose sensing complex is a first color when the concentration of glucose in the sweat of the individual is less than 1.8 mg/dL, and a second color when the concentration of glucose is greater than 1.8 mg/dL. These methods further comprise forming a spacer layer disposed over the substrate layer, wherein the spacer layer is formed to comprise a port that allows visualization of the glucose sensing complex in the substrate layer; and also forming a cover layer over the spacer layer, wherein the cover layer is formed to comprise a port that allows visualization of the glucose sensing complex in substrate layer.

These methods of making a glucose sensor can include forming other elements on the sensor, for example a wetness indicator that indicates when sufficient sweat has accumulated for the glucose sensing reaction; and/or a color indicator (e.g. a color chart/key) that shows a first color of the chromogen when the concentration of glucose is greater than 1.8 mg/dL; and/or a pH indicator that indicates the pH of the aqueous solution in which glucose is sensed. Optionally in these methods, a region of the substrate layer in which the glucose sensing complex is disposed is formed to comprise a preloaded concentration of glucose adapted to form a threshold concentration of glucose in an aqueous environment in which the glucose sensing complex is disposed. In certain embodiments of the invention, the method further comprises forming hydrophobic regions on the glucose sensor that are adapted to modulate the flow of sweat through the glucose sensor. Typically, the glucose sensor is formed to measure glucose in volumes of sweat that are between 5 microliters and 25 microliters; and/or to indicate when the concentration of glucose in the sweat of a user is greater than 1.8 mg/dL. Certain embodiments of the invention include the step of spotting a known concentration of glucose on the paper as a control (e.g. on the sensor or on the color chart), a spot that a user can wet and compare the results to that obtained from sweat.

Figure 3:
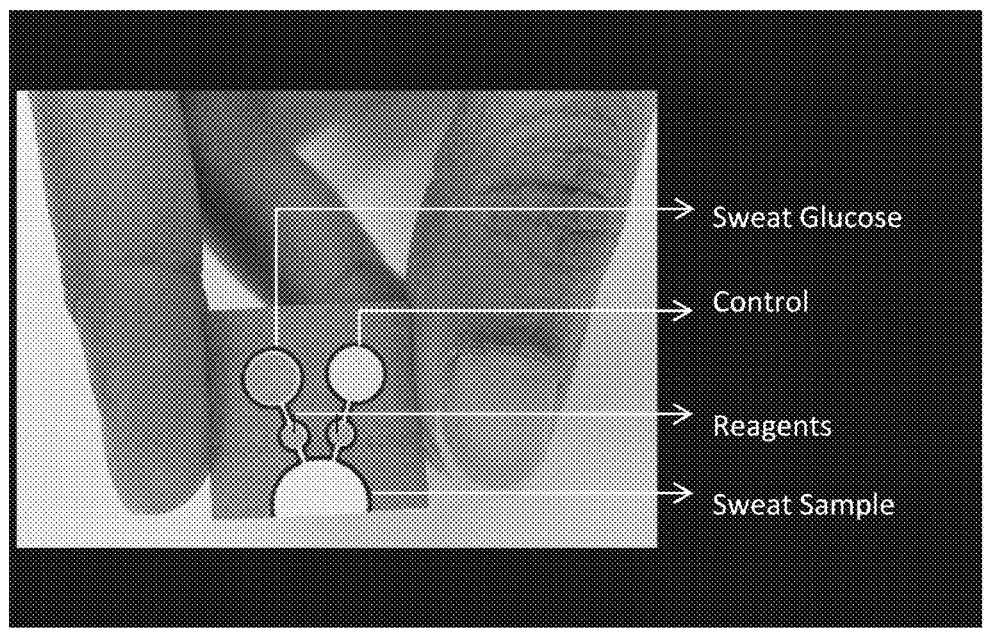
FIG. 3 provides a photograph of an embodiment of a sweat patch glucose sensor showing various elements of this sensor embodiment.
Figure 4:
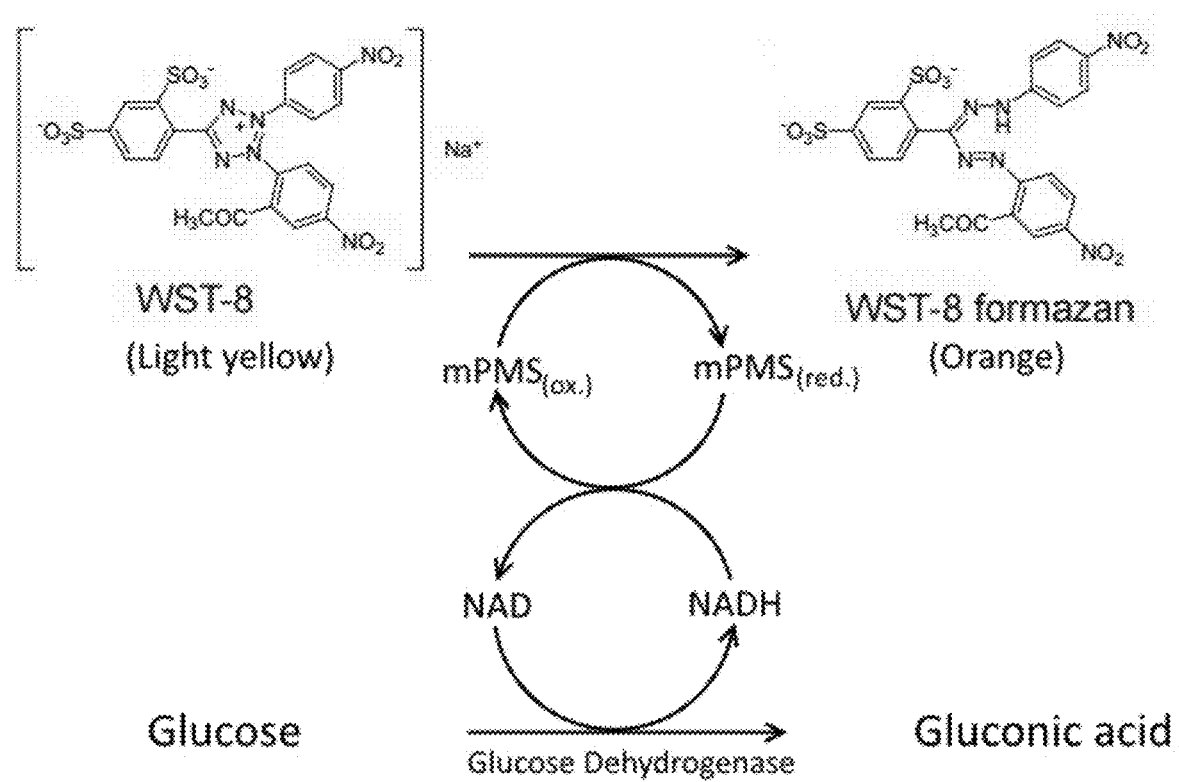
FIG. 4 provides a cartoon schematic of a glucose detection scheme using glucose dehydrogenase (GDH) enzyme, one where the chromogen is a water-soluble tetrazolium salt (e.g. WST-8).
Figure 5:
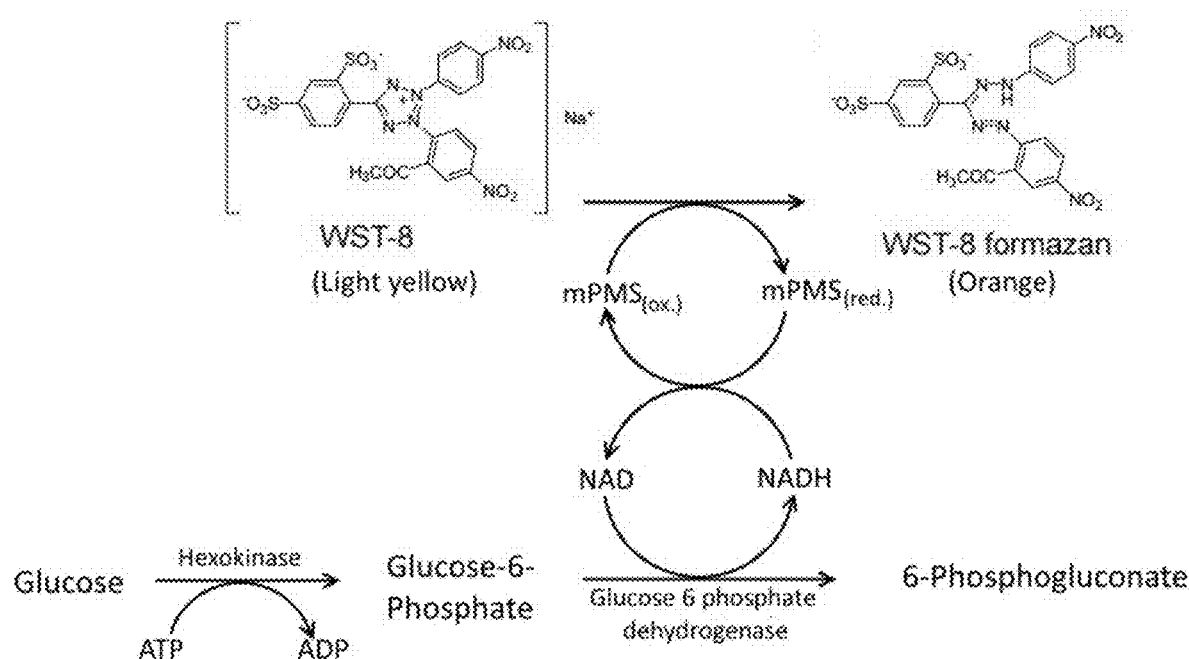
FIG. 5 provides a cartoon schematic of a glucose detection scheme using a hexokinase/glucose 6 phosphate enzyme system, one where the chromogen is a water-soluble tetrazolium salt (e.g. WST-8).
Figure 6A:
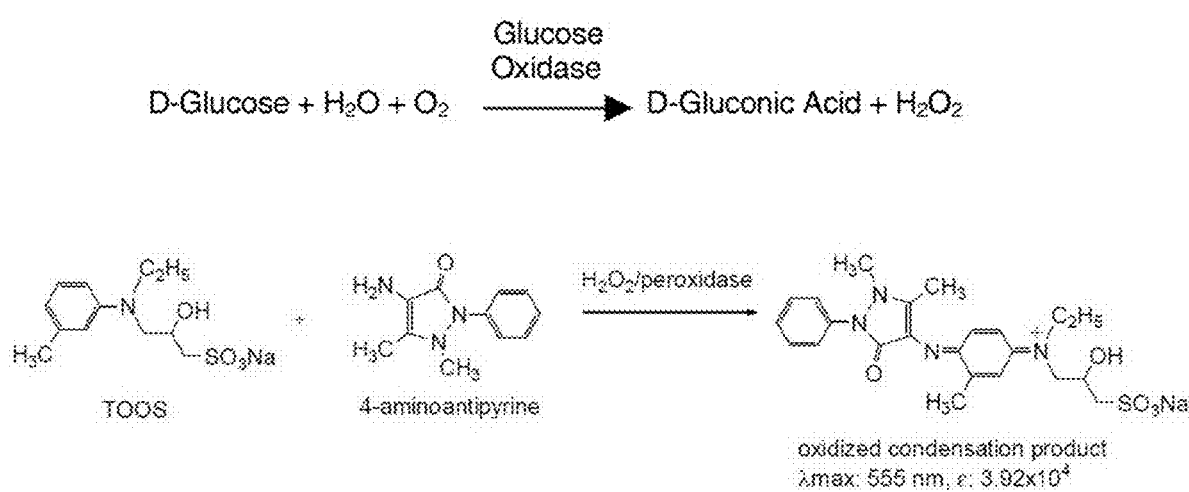
FIG. 6A provides a cartoon schematic of a glucose detection scheme using glucose oxidase enzyme, one where the chromogen is a Trinder's reagent dye N-Ethyl-N-(2-hydroxy-3-sulfopropyl)-3-methylaniline sodium salt dihydrate (TOOS)
Figure 6B:
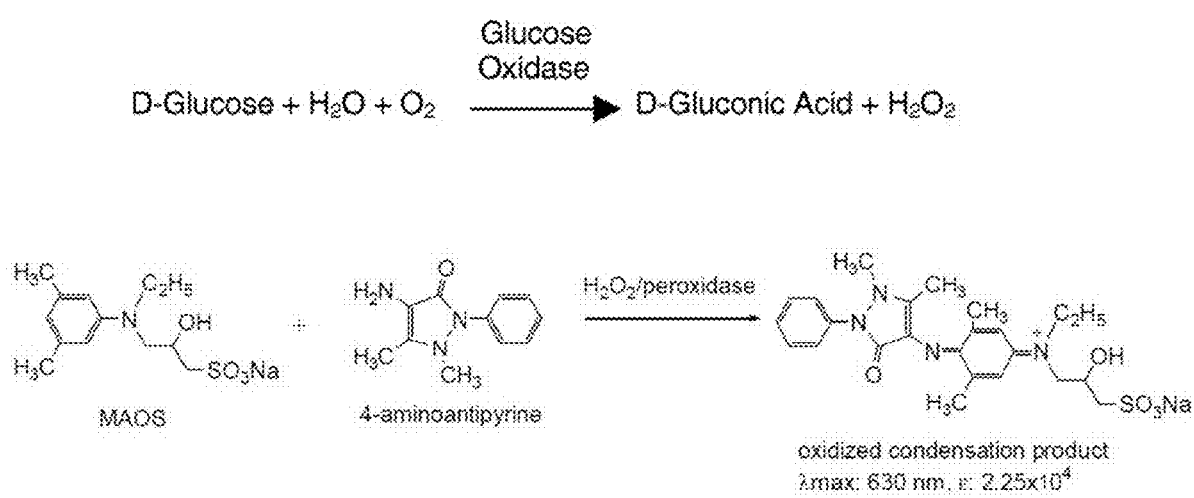
FIG. 6B provides a cartoon schematic of a glucose detection scheme using glucose oxidase enzyme, one where the chromogen is a Trinder's reagent dye N-Ethyl-N-(2-hydroxy-3-sulfopropyl)-3,5-dimethylaniline sodium salt monohydrate (MAOS).

In embodiments of the invention, fluid conduits may be fabricated using one or more hydrophobic materials (e.g. as aqueous barriers) to facilitate the flow of an aqueous solution through the sensor. For example, hydrophobic materials may be used to form the wall/barrier on either side of a channel on a substrate through which sweat fluid flows, as well as a reaction zone were the glucose sweat ultimately resides as glucose is sensed (see, e.g. FIG. 3). Hydrophobic materials may be used to repel sweat from the bottom surface of channel layer through the sensor (e.g. through an opening and into a hydrophilic reaction zone within the skin patch sensor that is surrounded by hydrophobic materials to form a barrier and/or delineate the reaction zone). The hydrophobic material may be selected based on flow properties, optical properties, conformability, viscoelasticity, flammability, toxicity, inertness, and/or the like. An example of a hydrophobic material that can be used in the manufacture of a conduit/channel is polydimethylsiloxane (PDMS). Hydrophobic and hydrophilic regions on a sensor (e.g. on the substrate layer) can also be fabricated by printing wax barrier on substrate (e.g. papers, plastics and the like) and subsequently heating to melt the wax to get wax into the pores of the substrates. A non-barrier hydrophilic reaction zone can be formed to hold the chemistry for detection of glucose. Layers of spacers and backing can be added to allow sample to be wicked to a reaction zone.

The sensor embodiments of the invention may have a single conduit/channel or any number of channels to contact the skin for sweat collection. Upon contacting the skin surface, the sensor deforms to contact as much skin as possible so that the channels may efficiently route sweat through the opening and to the reaction zone. Because certain channel features may be hydrophobic, certain embodiments of the invention can comprise a hydrophilic coating to attract the sweat into the sensor and reaction zone. Further, the opening may also be coated with one or more hydrophilic materials. Hydrophilic materials that may be used include, but are not limited to, glass, 2-hydroxyethyl methacrylate (HEMA), poly(oxyethylene) (POE), silicon dioxide, poly(ethylene glycol) (PEG), and polyacrylamide. In some variations in which the channel is formed of PDMS, surface modifications of the PDMS may be performed by, for example, oxygen plasma treatments, or UV-mediated grafting.

Hydrophobic and hydrophilic barriers can be created by other methods such as by spraying hydrophobic polymers (e.g. polydimethylsiloxane) on the substrate using a mask to cover the required hydrophilic regions. Hydrophobic and hydrophilic barriers can be created by printing wax with a wax printer, by paraffin stamped on paper, through the use of hydrogels (e.g. a silica gels on hydrophobic base material). Generally, hydrophobic and hydrophilic materials can be used to modify sensor elements and create hydrophobic pathways that direct the flow of sweat through the sensor (e.g. APTES surface modified on transparency sheets to create pathways). In this context, WO2010102294A1 discloses illustrative methods for doing so to create micropatterning paper based microfluidics (e.g. printing of a solid wax ink onto a paper substrate in a predetermined pattern defining an assay region to allow for the manufacture of microfluidic analytical sensor). The hydrophobic regions may be created in this manner (but not required if sensor is designed accordingly).

Optionally in embodiments of the invention, the glucose sensing complex and/or the colorimetric indicator (chromogen) is coupled to the substrate layer. For example, in some embodiments of the invention, the glucose sensing complex and/or the colorimetric indicator is immobilized using a poly(vinyl alcohol) (PVA) substituted with styrylpyridinium (SbQ), and/or a chitosan and/or a polyethyleneimine. In illustrative embodiments of the invention, the substrate can be porous paper, textile, porous hydrogels, and the like.

In a specific embodiment of the invention, the substrate layer is formed from high flow rate paper (e.g. akin to Kim wipe tissue paper), and the sensor includes one or more plastic spacers, a top cover (e.g. Tegaderm), and a bottom adhesive patch with a sweat sample port. The substrate layer paper consists of chemistry for glucose oxidase (enzyme+dye) such as dried buffer compounds to adjust sweat sample pH to 7.0-8.4. GOX enzyme is immobilized on substrate paper using PVA/SBQ and the chromophore/dye is TOOS. Immobilization chemistry can be utilized where the dye is immobilized on to the substrate to minimize the dye blotting and moving to the edges of the substrate. One example is use of ion exchange material like Polyethylene imine (PEI) coated on the substrate followed by the dye coating. Positive charges on the PEI will hold a negatively charged dye in place. A known amount of glucose can be added to the substrate and dried to ultimately create a more intense color in the chromogen by artificially increasing the glucose concentration in the environment in which the glucose sensing complex senses glucose (in a manner akin to "standard addition method" in analytical chemistry). A color reference chart can be disposed on the sensor to compare a color standard to the developed sample color. In addition, the sensors can be stored in and protected by light protected packaging.

Methods for measuring a glucose level from sweat are also provided. In general, methods for measuring a glucose level from sweat comprise collecting sweat from skin using a skin patch and measuring the amount of glucose within the volume of sweat. The skin patch may be attached to any location on the body covered by skin. Typically, however, the skin patch is placed on a fingertip, hand, or forearm as these areas have a higher density of sweat glands, are easily accessible, and are currently used by diabetic patients for blood glucose testing. The skin patch may be a skin patch as described herein and the predetermined volume of sweat may be about 5-25 microliters or any other suitable volume (e.g. 5-30 microliters, 5-40 microliters, 5-50 microliters or the like).

In some embodiments, the method also includes stimulating sweat production. Sweat may be generated via exercise, with for example, a sweat sample introduced into the sensor after a 15 minute workout. Sweat production may be simulated chemically, e.g., by delivering pilocarpine to the skin surface. The pilocarpine may be wiped onto the skin surface prior to attachment of the skin patch. Sweat may also be stimulated by delivering heat or one or more other forms of energy to the surface of the skin. The patch itself may comprise a physical, chemical, or mechanical mechanism of inducing a local sweat response. For example, the patch may comprise pilocarpine, alone or with a permeation enhancer, or may be configured for iontophoretic delivery. Similarly, the patch may comprise one or more chemicals capable of inducing a local temperature increase, thereby initiating a local sweat response. In a like manner, the patch may also comprise one or more heaters for sufficient localized heating of the skin surface to induce an enhanced local sweat response.

Yet another embodiment of the invention is a method of detecting hyperglycemia in an individual, comprising the steps of wiping skin of the individual to remove contaminants at a site at which the sensor will be adhered and then adhering a glucose sensor to the skin of the individual. The sensors used in these methods typically comprise an adhesive layer adapted to bond to skin on an individual, wherein the adhesive layer comprises an opening adapted to allow sweat to migrate from the skin of the individual to a glucose sensing complex within the glucose sensor, a substrate layer disposed over the adhesive layer and comprising a glucose sensing complex, wherein the substrate layer accumulates sweat that migrates from the skin of the individual in to the sensor (e.g. via conduits that direct the flow of sweat from the skin of a user to a reaction zone in which the glucose sensing complex is disposed). In such embodiments, the glucose sensing complex comprises an enzyme complex that reacts with glucose and comprises: glucose oxidase, glucose dehydrogenase or a hexokinase/glucose-6-phosphate complex and also a colorimetric indicator that changes color when glucose concentrations are when concentrations of glucose in sweat are greater than 1.8 mg/dL. In these embodiments, a spacer layer is disposed over the substrate layer, wherein the spacer layer comprises a port that allows visualization of the glucose sensing complex in the substrate layer; and a cover layer is disposed over the spacer layer, wherein the cover layer comprises a port that allows visualization of the glucose sensing complex in substrate layer. These methods then include allowing the individual to form sweat in amounts sufficient to measure glucose, and finally observing the colorimetric indicator to observe concentrations of glucose greater than 1.8 mg/dL. Optionally in these embodiments, a region of the substrate layer in which the glucose sensing complex is disposed comprises a preloaded concentration of glucose adapted to form a threshold concentration of glucose in the environment in which the glucose sensing complex senses glucose.

In these methods, the glucose sensor is adapted to detect glucose in the sweat of the individual, a body fluid which can evaporate very quickly. These methods can therefore further comprise disposing a layer over the sensor (a layer that is typically transparent), wherein the layer comprises an adhesive, and is formed from a material selected for its ability to inhibit the evaporation of sweat. In addition, in order to determine when the fixed volume of sweat is collected, the skin patch can include a wetness/volume indicator. In view of this, certain embodiments of the invention include additional elements that facilitate the user interface with the sensor, for example a wetness indicator that indicates when sufficient sweat has accumulated for the glucose sensing reaction.

Some embodiments of the invention can include a color key that indicates the expected color of the colorimetric indicator when concentrations of glucose in the sweat of the individual are at a certain level, for example when concentrations of glucose are greater than 1.8 mg/dL. Similarly, some embodiments of the invention can include a pH indicator that indicates the pH of the glucose sensing reaction. With such sensors, the methods can further comprise taking a photograph of the glucose sensing complex and the predetermined color indicator (and/or pH key) so as provide a computer readable comparison of the color of the colorimetric indicator (or pH) with that of the predetermined color indicator. For example, any color change can be visually compared with a color chart (e.g. a color chart disposed on the outside of the sensor), or the individual can use a smartphone to take an image and compare an obtained glucose signal to known standards. Alternatively, the background color of the sensor will represent the color equivalent for a diabetic patient (e.g. an orange color for blood glucose concentrations greater than 180 mg/dL).

Typically, glucose sensing occurs at room temperature or at body temperature. In certain embodiments of the invention, the sensor can be used like a swipe on fresh sweat. In this situation the sensor needs to be incubated for up to 10 minutes prior to results comparison as the reaction time for full color development is typically 5-8 minutes in solution and may be longer in certain embodiments of the invention. Alternatively, the sensor can be worn on the skin at body temperature, in this case the incubation time could be less than 10 minutes. During reaction time, evaporation should be avoided and a top sheet of a clear material that inhibits evaporation can be disposed over the whole sensor to do so.

In an illustrative embodiment of the invention, a user can clean a skin surface with an isopropyl alcohol wipe or a damp cloth. The user can then peel adhesive cover off the bottom of the sensor and stick the sensor on the skin. The user can then wait until a wetness indicator changes color to indicate sufficient wetness. Optionally, the user can then remove an element (e.g. a barrier element) to activate the patch sensor (alternatively this can occur without a user step). The user can then wait for 5-10 mins. The user can then compare the observed color with standard color chart/key (optionally using a smartphone having an application designed to analyze the color change). The user can then discard the sensor.

In one exemplary embodiment of the invention, the glucose sensing complex comprises glucose oxidase, and the colorimetric indicator comprises a Trinder reagent comprising an aminoantipyrine (such as 4-aminoantipyrine or the like) and a phenol (such as p-hydroxybenzene or the like). In another exemplary embodiment of the invention, the glucose sensing complex comprises glucose dehydrogenase and the colorimetric indicator comprises a water-soluble tetrazolium salt, and the method further comprises combining the glucose sensing complex with nicotinamide adenine dinucleotide (NAD) and a 1-methoxy-5-methylphenazium methylsulfate. In another exemplary embodiment of the invention, the glucose sensing complex comprises a hexokinase/glucose-6-phosphate complex and the colorimetric indicator comprises a water-soluble tetrazolium salt, and the method further comprises combining the glucose sensing complex with nicotinamide adenine dinucleotide (NAD) and a 1-methoxy-5-methylphenazium methylsulfate.

Certain embodiments of the invention include combining the glucose sensing enzyme complex with a predefined concentration of buffering compounds adapted to modulate the pH of an aqueous environment as the glucose sensing complex senses glucose (e.g. so as to optimize the pH for the specific enzyme used in the sensing complex). Embodiments of the invention can also incorporate an electron donor compound such as sodium formate, dextrose, glycerin and glycerol in conjunction with a fixing agent such as ferricyanide (Prussian blue color) or Fehling's solution (copper (II) sulfate and potassium sodium tartrate made in strong alkali).

In typical embodiments of the invention, the sensor is a single use sensor that can be applied onto the skin to measure sweat glucose. One can ship these sensors via mailer to generally healthy patients who have a pre-disposition to diabetes. Users then test themselves with a sample of sweat at their convenient time. A user can then compare the results of the glucose color reaction visually or a smart phone camera to a standard color chart. If the glucose range is above normal then the user is considered at-risk for diabetes and is recommended for further testing and treatment. In embodiments of the invention, the sensor does not provide a specific glucose value and instead only provides a qualitative indication the glucose is above the normal range and in the range of hyperglycemia.

The sensors of the invention can be used in a variety of contexts. For example, to facilitate Diabetes Prevention Program (DPP) tracking and motivation, DPP companies (like Canary Health, YMCA) can mail the sensor to potential customers to help them identify hyperglycemia, and track their glucose range (e.g. for data significant to improved diet and exercise regimens). This can provide motivation to users to keep them enrolled in a DPP program (e.g. users can modify their calorie in-take and exercise intensity based on sensor determined glucose concentrations). In some embodiments of the invention, the sensor is a 3-D multi-layered sweat glucose detection patch, one where each layer provides a glucose measurement at a different time (i.e. over the course of a few hours). Users can, for example, peel the sensor and record the time in range over the course of a day of wear (e.g. every 6 hours). The tracking of "time in range" can be done via a smart phone. In certain embodiments of the invention, a health care provider can use the sensor to track diet and exercise.

Figure 7:
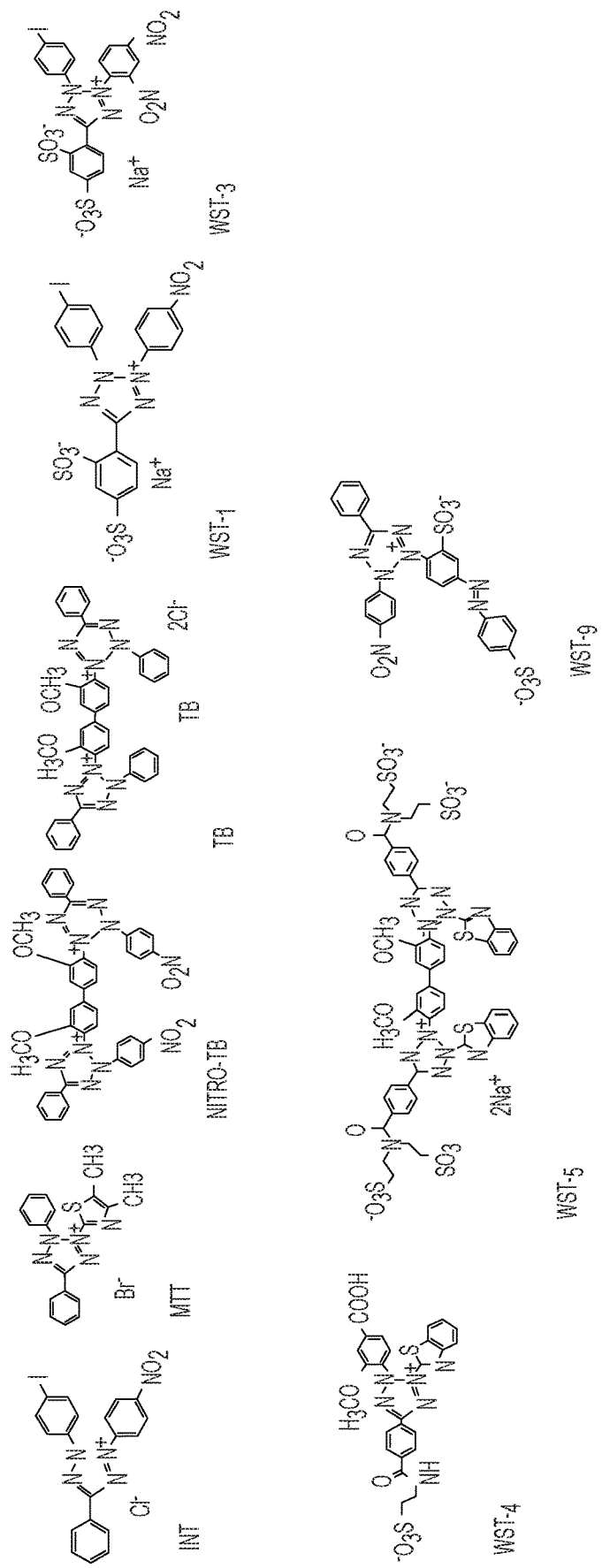
FIG. 7 provides cartoon schematics of chromogens (colorimetric indicators) useful in embodiments of the invention.
Figure 8:
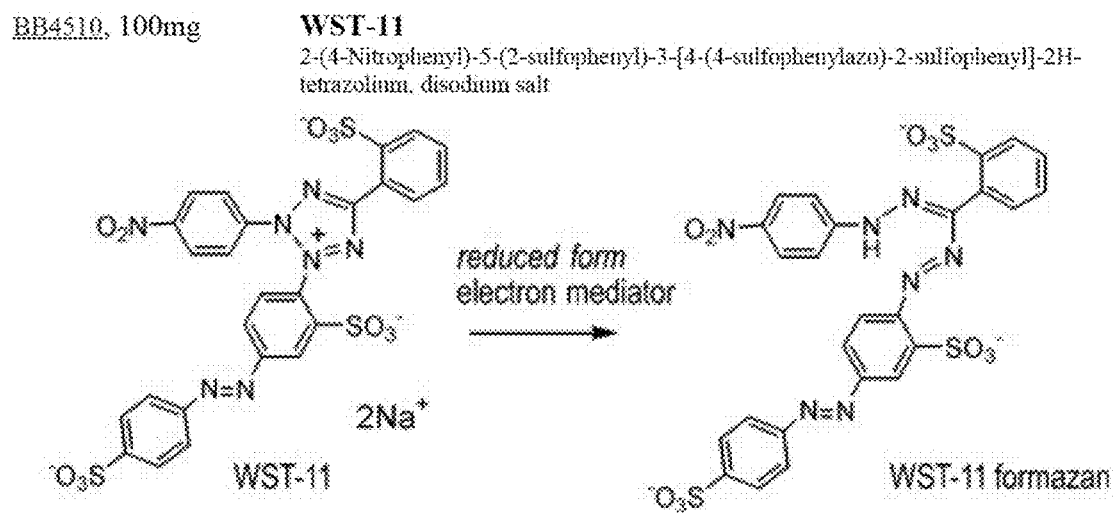
FIG. 8 provides cartoon schematics of chromogens useful in embodiments of the invention.
Figure 9:
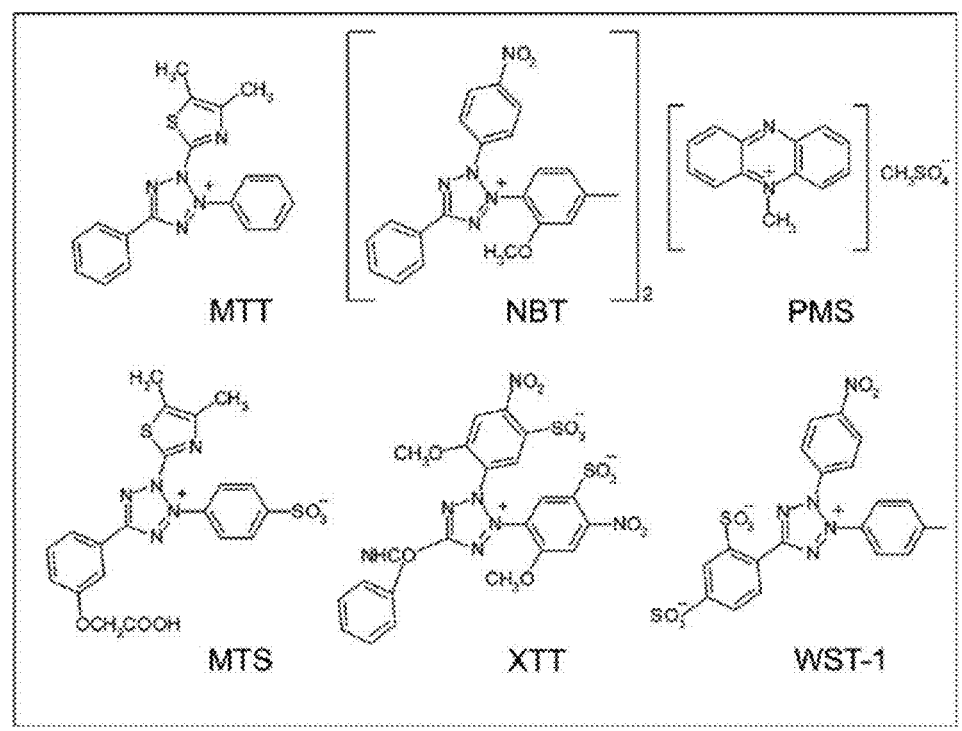
FIG. 9 provides cartoon schematics of chromogens useful in embodiments of the invention.
Figure 10:
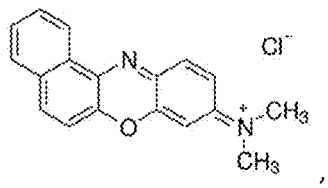
FIG. 10 provides cartoon schematics of mediators useful in embodiments of the invention.
Figure 10:
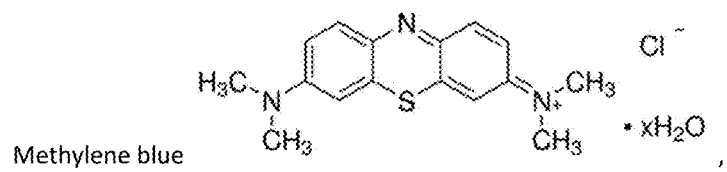
Figure 10:
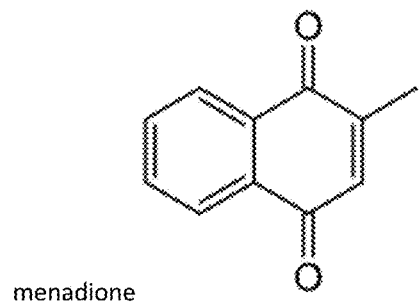
Figure 11:
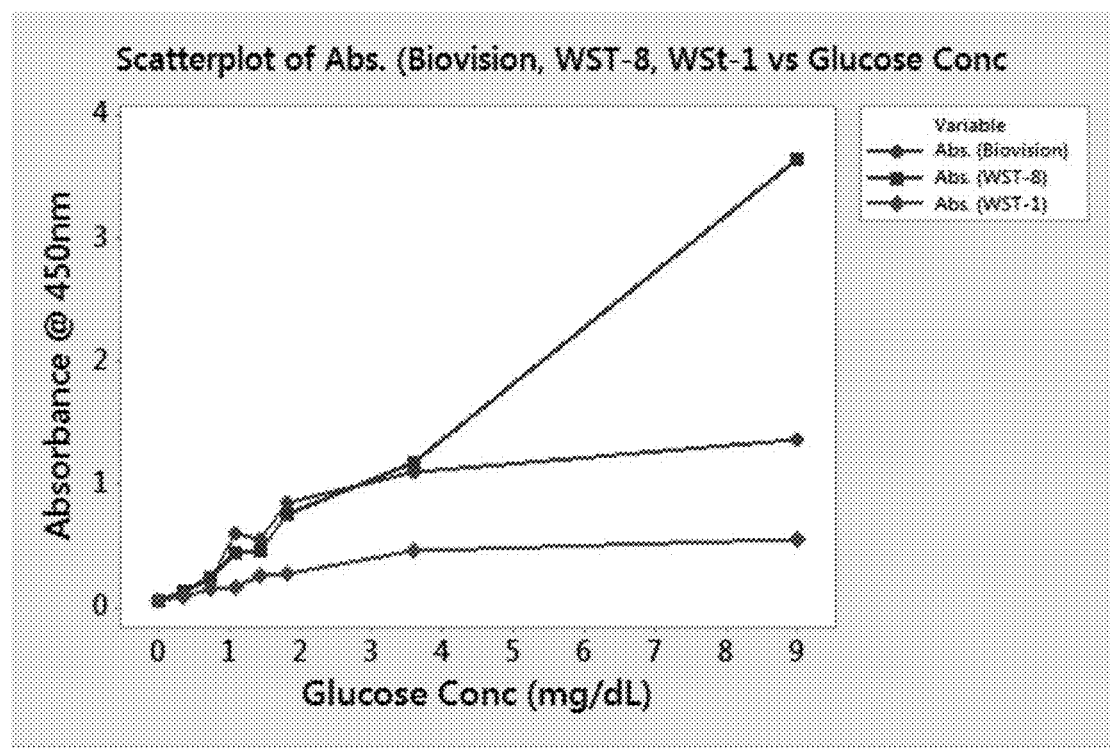
FIG. 11 provides a graph of data showing the measurement of glucose using sweat patch glucose sensor embodiments having different chromogens (e.g. WST-1, WST-8).
Figure 12:
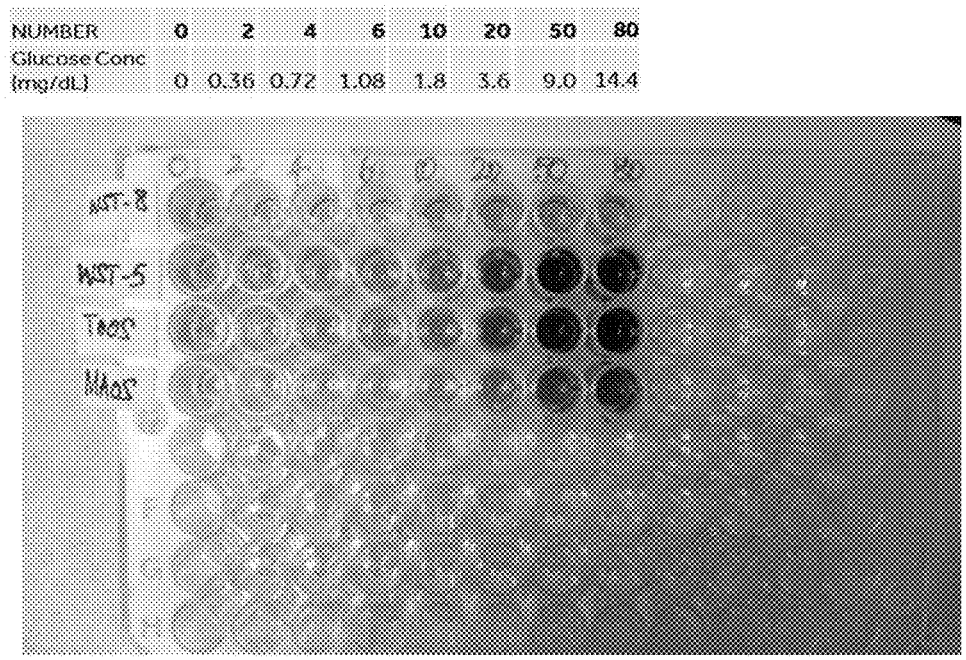
FIG. 12 provides a photograph of data generated in a study of glucose detection using a glucose sensing complex comprising glucose oxidase and the associated coloration of various chromogens (e.g. WST-5, WST-8, TAOS and MAOS).

Another embodiment of the invention is a composition of matter comprising a glucose sensing enzyme complex that reacts with glucose and comprises: glucose oxidase, glucose dehydrogenase or a hexokinase/glucose-6-phosphate complex as well as a colorimetric indicator (see, e.g. the chromogens in FIGS. 7-9) that changes color following reaction of glucose with the enzyme complex; and also a predefined concentration of glucose adapted to form a threshold concentration of glucose in an aqueous environment as the glucose sensing complex senses glucose. Optionally, the glucose sensing complex and/or the colorimetric indicator to a porous substrate. Typically, these elements are disposed in locations and amounts so that the glucose sensing complex is adapted to determine the concentrations of glucose in aqueous solutions having a volume between 5 and 25 microliters. In certain embodiments of the invention, the glucose sensing enzyme complex and/or the colorimetric indicator is coupled to a substrate (e.g. a porous hydrophilic substrate).

In certain embodiments of the invention, the colorimetric indicator exhibits a first color when the glucose sensing enzyme complex is disposed in solutions having concentrations of glucose below a certain threshold, for example less than 1.8, 1.5, or 1.25 mg/dL, and the colorimetric indicator exhibits a second color when disposed in solutions having concentrations above a certain threshold, for example a concentration of glucose greater than 1.5, 1.6, 1.8 or 2.0 mg/dL. In some embodiments of the invention, the glucose sensing complex comprises glucose oxidase, and the colorimetric indicator comprises a Trinder reagent comprising an aminoantipyrine (such as 4-aminoantipyrine) and a phenol (p-hydroxybenzene). In other embodiments of the invention, the glucose sensing complex comprises glucose dehydrogenase, the composition further comprises a nicotinamide adenine dinucleotide (NAD) and a 1-methoxy-5-methylphenazium methylsulfate, and the colorimetric indicator comprises a water-soluble tetrazolium salt. In other embodiments of the invention, the glucose sensing complex comprises a hexokinase/glucose-6-phosphate complex, the composition further comprises a nicotinamide adenine dinucleotide (NAD) and a 1-methoxy-5-methylphenazium methylsulfate, and the colorimetric indicator comprises a water-soluble tetrazolium salt.

A related embodiment of the invention is a method of making a composition that measures glucose concentrations between 0 mg/dL and 5 mg/dL in volumes between 5-25 microliters by exhibiting a first color when disposed in aqueous solutions having a first concentration of glucose, and a second color when disposed in aqueous solutions having a second higher concentration of glucose, the method comprising combining together a glucose sensing enzyme complex that reacts with glucose and comprises: glucose oxidase, glucose dehydrogenase or a hexokinase/glucose-6-phosphate complex; and a colorimetric indicator that changes color following reaction of glucose with the enzyme complex. Optionally the methods further comprise combining the glucose sensing enzyme complex with a predefined concentration of glucose adapted to form a threshold concentration of glucose in an aqueous environment as the glucose sensing complex senses glucose. Such embodiments of the invention can include the step of adding sweat to the glucose sensing complex.

Various methods may be used to manufacture the skin patch sensors of the invention. In some embodiments, the layers are each manufactured separately and later assembled. In other embodiments, the layers may be assembled during manufacture, for example, one layer may be fabricated directly on top of or beneath another layer. The layers may be cut, molded, or otherwise fabricated. In some embodiments, micro-molding techniques and/or photolithography techniques may be used. In other embodiments, other suitable techniques, such as micro-machining, may be used.

In some embodiments, the layers may be treated or modified prior to being assembled. The layers may, for example, be at least partially modified to change the hydrophobic or hydrophilic nature of the materials used. For example, a hydrophilic coating may be applied to at least a portion of a layer fabricated from a hydrophobic material such as PDMS. Hydrophilic materials that may be used include, but are not limited to, glass, 2-hydroxyethyl methacrylate (HEMA), poly(oxyethylene) (POE), silicon dioxide, poly(ethylene glycol) (PEG), and polyacrylamide. Surface modifications of PDMS may also be performed by, for example, oxygen plasma treatments and/or UV-mediated grafting. Additionally, as discussed above one or more features may be added to the layers using conventional techniques. As discussed above, these features may include channels, reaction zones, spacers, transparent layers, buffer, analytes or enzyme coatings (e.g., glucose and glucose oxidase), as well visual indicators to facilitate the user interface (e.g. indicators of glucose concentrations, wetness or pH) or the like.

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The invention claimed is:

1. A composition of matter comprising:
   a glucose sensing enzyme complex that reacts with glucose and comprises:
   glucose oxidase, glucose dehydrogenase or a hexokinase/glucose-6-phosphate complex;
   a colorimetric indicator that changes color following reaction of glucose with the glucose sensing enzyme complex; and
   a predefined concentration of glucose adapted to form a threshold concentration of glucose in an aqueous environment as the glucose sensing enzyme complex senses glucose; wherein:
   the composition is disposed within a porous substrate;
   the porous substrate comprises at least one channel in operable contact with the glucose sensing enzyme complex;
   the porous substrate is coupled to a layer of an adhesive adapted to adhere to human skin;
   the layer of the adhesive comprises an opening adapted to allow sweat to flow from human skin into the porous substrate, wherein the opening is operably connected to the at least one channel; and
   the opening, the at least one channel and the glucose sensing complex are disposed in the composition such that concentrations of glucose can be sensed in sweat that flows from human skin into the opening and through the at least one channel to the glucose sensing enzyme complex.

2. The composition of claim 1, wherein the glucose sensing enzyme complex is adapted to determine the concentrations of glucose in sweat having a volume between 5 and 25 microliters.

3. The composition of claim 1, wherein the glucose sensing enzyme complex and/or the colorimetric indicator is immobilized in the porous substrate using:
   a poly(vinyl alcohol) (PVA) substituted with styrylpyridinium (SbQ);
   a chitosan; and/or
   polyethylenimine.

4. The composition of claim 1, wherein the colorimetric indicator exhibits a first color when the glucose sensing enzyme complex is disposed in solutions having concentrations of glucose less than 1.8 mg/dL, and the colorimetric indicator exhibits a second color when disposed in solutions having concentrations of glucose greater than 1.8 mg/dL.

5. The composition of claim 1, further comprising a predefined concentration of buffering compounds adapted to modulate the pH in an aqueous environment as the glucose sensing enzyme complex senses glucose.

6. The composition of claim 1, further comprising human sweat.

7. The composition of claim 1, wherein the glucose sensing enzyme complex comprises glucose oxidase, and the colorimetric indicator comprises a Trinder reagent comprising 4-aminoantipyrine and p-hydroxybenzene.

8. A composition of matter comprising:
(a) a glucose sensing enzyme complex that reacts with glucose and comprises:
glucose oxidase, glucose dehydrogenase or a hexokinase/glucose-6-phosphate complex;
(b) a colorimetric indicator that changes color following reaction of glucose with the glucose sensing enzyme complex;
(c) a predefined concentration of glucose adapted to form a threshold concentration of glucose in an aqueous environment as the glucose sensing enzyme complex senses glucose;
(d) buffering compounds that increase the pH of sweat:
(e) a porous substrate; and
(f) an adhesive composition adapted to adhere to human skin;
wherein:
(a)-(d) are disposed within the porous substrate;
the porous substrate is coupled to a layer of the adhesive composition adapted to adhere to human skin; and
the layer of the adhesive composition adapted to adhere to human skin comprises an opening adapted to allow sweat to flow from skin to (a)-(d).

9. The composition of claim 8, wherein the porous substrate comprises hydrophilic regions and hydrophobic regions disposed within the porous substrate so as to modulate the flow of sweat from skin to the glucose sensing enzyme complex.

10. The composition of claim 9, wherein the porous substrate comprises an adsorbent material adapted to wick sweat from skin to the glucose sensing enzyme complex.

11. The composition of claim 10, further comprising a cover layer disposed over the colorimetric indicator, wherein the cover layer comprises a port adapted to allow the colorimetric indicator to be visualized.

12. The composition of claim 11, further comprising a spacer layer disposed between the cover layer and the porous substrate, wherein the spacer layer comprises a port adapted to allow the colorimetric indicator to be visualized.

13. The composition of claim 11, wherein the cover layer further comprises a color key showing an expected color when concentrations of glucose in sweat are greater than 1.8 mg/dL.

14. The composition of claim 11, wherein the cover layer further comprises a wetness indicator that indicates when amounts of sweat sufficient to sense glucose have accumulated in the porous substrate.

15. The composition of claim 11, wherein the cover layer further comprises a pH indicator that indicates the pH of the glucose sensing reaction.

16. The composition of claim 8, wherein the glucose sensing enzyme complex is disposed at a location in the porous substrate and coupled to the layer of adhesive composition in an orientation such that when the composition is adhered to an individual, sweat flows from skin of the individual to the glucose sensing enzyme complex so that the composition non-invasively senses glucose present in sweat.

17. A composition of matter comprising:
a glucose sensing enzyme complex that reacts with glucose and comprises: glucose oxidase, glucose dehydrogenase or a hexokinase/glucose-6-phosphate complex;
a colorimetric indicator that changes color following reaction of glucose with the enzyme complex; and
a predefined concentration of glucose adapted to form a threshold concentration of glucose in an aqueous environment as the glucose sensing enzyme complex senses glucose;
wherein:
the composition is disposed within a porous substrate;
the porous substrate comprises at least one channel in operable contact with the glucose sensing enzyme complex;
the porous substrate comprises buffering compounds that increase the pH of human sweat;
the porous substrate is coupled to a layer of an adhesive adapted to adhere to human skin;
the layer of the adhesive comprises an opening adapted to allow sweat to flow from human skin into the porous substrate, wherein the opening is operably connected to the at least one channel; and
the opening, the at least one channel, the buffering compounds and the glucose sensing complex are disposed in the porous substrate such that concentrations of glucose can be sensed in volumes between 5 and 25 microliters of sweat that flow from human skin into the opening and through the at least one channel to the buffering compounds and the glucose sensing enzyme complex, wherein the buffering compounds increase the pH of human sweat that contacts the glucose sensing enzyme complex.

* * * * *